United States Patent
Zou et al.

(10) Patent No.: US 12,011,277 B2
(45) Date of Patent: Jun. 18, 2024

(54) RR INTERVAL ECG DATA DISTRIBUTION DISPLAY METHOD AND DEVICE, COMPUTER EQUIPMENT AND MEDIUM

(71) Applicant: SHENZHEN BIOCARE BIO-MEDICAL EQUIPMENT CO., LTD., Guangdong (CN)

(72) Inventors: JiJie Zou, Guangdong (CN); XiaoLin Yu, Guangdong (CN); JieXin Hong, Guangdong (CN)

(73) Assignee: SHENZHEN BIOCARE BIO-MEDICAL EQUIPMENT CO., LTD., Guangdong (CN)

(*) Notice: Subject to any disclaimer, the term of this patent is extended or adjusted under 35 U.S.C. 154(b) by 330 days.

(21) Appl. No.: 17/333,039

(22) Filed: May 28, 2021

(65) Prior Publication Data
US 2021/0282691 A1    Sep. 16, 2021

Related U.S. Application Data

(63) Continuation of application No. PCT/CN2020/119955, filed on Oct. 9, 2020.

(30) Foreign Application Priority Data

Dec. 27, 2019  (CN) .......................... 201911377443.1

(51) Int. Cl.
*A61B 5/352*    (2021.01)
*A61B 5/00*     (2006.01)
(Continued)

(52) U.S. Cl.
CPC .............. *A61B 5/352* (2021.01); *A61B 5/339* (2021.01); *A61B 5/7264* (2013.01)

(58) Field of Classification Search
CPC ........ A61B 5/352; A61B 5/339; A61B 5/7264
(Continued)

(56) References Cited

U.S. PATENT DOCUMENTS 3,880,147 A    4/1975  Gruenke et al.
5,628,326 A    5/1997  Arand et al.
(Continued)

FOREIGN PATENT DOCUMENTS

CN    102389303    3/2012
CN    105902263    8/2016
(Continued)

OTHER PUBLICATIONS

Badilini, et al., "Holter Monitoring for QT", Cardiac Safety of Noncardiac Drugs: Practical Guidelines for Clinical Research and Drug Development. Netherlands: Humana Press., Chapter 9, p. 170 (Year: 2007).*
(Continued)

*Primary Examiner* — James M Kish
*Assistant Examiner* — Paroma Mukhopadhyay
(74) *Attorney, Agent, or Firm* — JCIP GLOBAL INC.

(57) ABSTRACT

The present invention discloses an RR interval ECG data distribution display method. The RR interval ECG data distribution display method includes: extracting an RR interval from a dynamic electrocardiogram, and dividing the RR interval according to the preset time interval to obtain N sub-RR intervals; obtaining the ECG data of the RR interval, wherein the ECG data includes at least two heartbeat types and the number of heartbeats corresponding to each of the heartbeat types; traversing the ECG data of each of the sub-RR intervals, and performing the cumulative summation operation on the number of heartbeats corresponding to the same heartbeat type to obtain the number of heartbeats of each heartbeat type in the N sub-RR intervals; and display-
(Continued)

ing the number of heartbeats of each heartbeat type and the heartbeat types in the N sub-RR intervals in the form of a distribution diagram.

9 Claims, 9 Drawing Sheets

(51) Int. Cl.
    *A61B 5/339*     (2021.01)
    *A61B 5/349*     (2021.01)
    *A61B 5/364*     (2021.01)

(58) Field of Classification Search
    USPC .......................................................... 600/521
    See application file for complete search history.

(56) References Cited

U.S. PATENT DOCUMENTS

| | | | | |
|---|---|---|---|---|
| 7,657,307 | B2 * | 2/2010 | Van Dam | A61B 5/352 600/512 |
| 8,323,189 | B2 * | 12/2012 | Tran | A61B 5/1112 600/300 |
| 9,326,697 | B2 * | 5/2016 | Linker | A61B 5/333 |
| 2002/0151806 | A1 | 10/2002 | Starobin et al. | |
| 2009/0216141 | A1 * | 8/2009 | Fischell | A61B 5/0031 600/509 |
| 2013/0296680 | A1 * | 11/2013 | Linker | A61B 5/346 600/391 |
| 2015/0164358 | A1 * | 6/2015 | Moorman | A61B 5/374 600/521 |
| 2018/0256059 | A1 * | 9/2018 | Perschbacher | A61B 5/7232 |
| 2020/0060562 | A1 * | 2/2020 | Lin | A61B 5/02208 |
| 2021/0353166 | A1 * | 11/2021 | Sirendi | G16H 50/20 |

FOREIGN PATENT DOCUMENTS

| | | | |
|---|---|---|---|
| CN | 105997054 | | 10/2016 |
| CN | 107358196 | | 11/2017 |
| CN | 107456227 | | 12/2017 |
| CN | 107495960 | | 12/2017 |
| CN | 107951485 | | 4/2018 |
| CN | 108403105 | | 8/2018 |
| CN | 109124620 | | 1/2019 |
| CN | 109770893 | | 5/2019 |
| CN | 110522440 | | 12/2019 |
| CN | 110693483 | | 1/2020 |
| CN | 111053551 | | 4/2020 |
| EP | 0316800 | A2 * | 5/1989 |
| EP | 1322223 | | 5/2007 |
| JP | 2007000357 | A * | 1/2007 |
| WO | 2010096478 | | 8/2010 |
| WO | WO-2017172271 | A1 * | 10/2017 ......... A61B 5/02405 |

OTHER PUBLICATIONS

Badilini, et al., "Holter Monitoring for QT", Cardiac Safety of Noncardiac Drugs: Practical Guidelines for Clinical Research and Drug Development. Netherlands: Humana Press., Chapter 9, p. 167-185 (Year: 2007) (Year: 2007).*
Xiaolin, Yu, "Analysis and reporting methods of electrocardiogramanges", Journal of Practical Electrocardiology, vol. 21, No. 5, with English abstract, Oct. 2011, pp. 340-350.
Chen, Zhibo et al., "Automatic detection and classification of atrial fibrillation using RR intervals and multi-eigenvalue", Journal of Biomedical Engineering, vol. 35, No. 4, with English abstract, Aug. 2018, pp. 550-556.
Jintao, Xiang, "Clinical application of electrocardiogramacattergram", Chinese Journal of Cardiac Pacing and Electrophysiology, vol. 33, No. 3, with English abstract, Jun. 2019, pp. 197-201.
Dai, Xiang et al., "Application of modified template matching method based on R-R interval in electrocardiogram automatic diagnosis", Biomedical Engineering and Clinical Medicine, vol. 19, No. 3, with English abstract, Jun. 2015, pp. 225-228.
Kartika, Resiandi et al., "Detection of Atrial Fibrillation Disease Based on Electrocardiogram Signal Classification Using RR Interval and K-Nearest Neighbor", 2018 6th International Conference on Information and Communication Technology (ICoICT), May 2018, pp. 501-506.
Zhou, Qunyi, "The Electrocardiogram Classification Research on Electrocardiogram RR Interval Variation", 2009 Second International Symposium on Computational Intelligence and Design, Dec. 2009, pp. 497-500.
Jie, Lian et al., "A simple method to detect atrial fibrillation using RR intervals", The American journal of cardiology, vol. 107, Issue 10, May 2011, pp. 1494-1497.
Faust, Oliver et al., "Automated detection of atrial fibrillation using long short-term memory network with RR Interval signals" Computers in biology and medicine, vol. 102, Jul. 2018, pp. 1-18.
"International Search Report (Form PCT/ISA/210) of PCT/CN2020/119955," mailed on Jan. 4, 2021, pp. 1-5.
"Office Action of China Counterpart Application", issued on Apr. 12, 2021, p. 1-p. 8.
"Office Action of China Counterpart Application", issued on Jun. 9, 2021, p. 1-p. 5.

* cited by examiner

RR INTERVAL ECG DATA DISTRIBUTION DISPLAY METHOD AND DEVICE, COMPUTER EQUIPMENT AND MEDIUM

CROSS-REFERENCE TO RELATED APPLICATION

This application is a continuation of PCT application No. PCT/CN2020/119955, filed on Oct. 9, 2020, which claims the priority benefit of China application no. 201911377443.1, filed on Dec. 27, 2019. The patent application is hereby incorporated by reference in its entirety.

BACKGROUND

Technical Field

Embodiments of the present disclosure relates to the technical field of electrocardiogram editing, in particular to an RR interval electrocardiography (ECG) data distribution display method and device, computer equipment and a medium.

Description of Related Art

A dynamic electrocardiogram analysis system uses a portable recorder to continuously collect the ECG data information of a human body in the natural state for 24 hours or more; and the ECG data information is processed, analyzed, replayed, and printed through computer software to assist doctors in analyzing reports. The RR interval is the time limit between two adjacent R waves in the QRS wave complex on an electrocardiogram. The normal RR interval should be between 0.6 second and 1.0 second. The RR interval of less than 0.6 second indicates tachycardia; and the RR interval of greater than 1.0 second indicates bradycardia. Arrhythmia, atrial fibrillation, conduction block and the like can be identified through the RR interval. The RR interval is an important parameter for clinical diagnosis of the dynamic electrocardiogram. Currently, in analytical applications of the dynamic electrocardiogram, RR interval analysis tools are basically divided into two types: an RR interval histogram and an RR interval scatter plot. The RR interval histogram is used for counting and displaying the number of heartbeats in a fixed interval of each RR interval, and shown in a bar chart. In the RR interval scatter plot, two adjacent RR intervals are taken as coordinate points in a two-dimensional coordinate system, and all these points are drawn into a graph to form a scatter plot. Although these two types of RR interval analysis tools can reflect the distribution of RR intervals, they only show statistics in the numerical sense of the RR interval graphically, which is not conducive to discovering the relationship between certain heart rhythm attributes in the frequency distribution, such as the early linkage of a variety of arrhythmia.

SUMMARY

The technical problem to be solved by the present disclosure is to provide an RR interval ECG data distribution display method and device capable of visually displaying RR interval heartbeat information to improve the efficiency of identifying abnormal heart rhythm events, computer equipment, and a medium.

The RR interval ECG data distribution display method is characterized by comprising the following steps of:

extracting the RR interval from a dynamic electrocardiogram, and dividing the RR interval according to a preset time interval to obtain N sub-RR intervals, wherein N is a natural number greater than 1;

obtaining the ECG data of the RR interval, wherein the ECG data includes at least two heartbeat types and the number of heartbeats corresponding to each of the heartbeat types;

traversing the ECG data of each of the sub-RR intervals, and performing the cumulative summation operation on the number of heartbeats corresponding to the same heartbeat type to obtain the number of heartbeats of each heartbeat type in the N sub-RR intervals;

and displaying the number of heartbeats of each heartbeat type and the heartbeat types in the N sub-RR intervals in the form of a distribution diagram.

The RR interval ECG data distribution display device includes:

a dividing module, used for extracting the RR interval from the dynamic electrocardiogram, and dividing the RR interval according to a preset time interval to obtain the N sub-RR intervals, wherein N is a natural number greater than 1;

an obtaining module, used for obtaining the ECG data of the RR interval, wherein the ECG data includes the at least two heartbeat types and the number of heartbeats corresponding to each of the heartbeat types;

a calculation module, used for traversing the ECG data of each of the sub-RR intervals, and performing the cumulative summation operation on the number of heartbeats corresponding to the same heartbeat type to obtain the number of heartbeats of each heartbeat type in the N sub-RR intervals; and a display module, used for displaying the number of heartbeats of each heartbeat type and the heartbeat types in the N sub-RR intervals in the form of the distribution diagram.

The computer equipment includes a memory and a processor; the memory stores a computer program; and when the computer program is executed by the processor, the processor executes the following steps of:

extracting the RR interval from the dynamic electrocardiogram, and dividing the RR interval according to a preset time interval to obtain the N sub-RR intervals, wherein N is a natural number greater than 1;

obtaining the ECG data of the RR interval, wherein the ECG data includes the at least two heartbeat types and the number of heartbeats corresponding to each of the heartbeat types;

traversing the ECG data of each of the sub-RR intervals, and performing the cumulative summation operation on the number of heartbeats corresponding to the same heartbeat type to obtain the number of heartbeats of each heartbeat type in the N sub-RR intervals;

and displaying the number of heartbeats of each heartbeat type and the heartbeat types in the N sub-RR intervals in the form of the distribution diagram.

The computer readable medium stores the computer program; and when the computer program is executed by the processor, the processor executes the following steps of:

extracting the RR interval from the dynamic electrocardiogram, and dividing the RR interval according to a preset time interval to obtain N sub-RR intervals, wherein N is a natural number greater than 1;

obtaining the ECG data of the RR interval, wherein the ECG data includes the at least two heartbeat types and the number of heartbeats corresponding to each of the heartbeat types;

traversing the ECG data of each of the sub-RR intervals, and performing the cumulative summation operation on the number of heartbeats corresponding to the same heartbeat type to obtain the number of heartbeats of each heartbeat type in the N sub-RR intervals;

and displaying the number of heartbeats of each heartbeat type and the heartbeat types in the N sub-RR intervals in the form of the distribution diagram.

The embodiments of the present application have the following beneficial effects:

according to the above RR interval ECG data distribution display method and device, the computer equipment and the storage medium, the N sub-RR intervals are obtained by extracting the RR interval from the dynamic electrocardiogram, and dividing the RR interval according to a preset time interval; the ECG data of the RR interval is obtained, and includes the at least two heartbeat types and the number of heartbeats corresponding to each of the heartbeat types; the ECG data of each of the sub-RR intervals is traversed, and the cumulative summation operation is performed on the number of heartbeats corresponding to the same heartbeat type to obtain the number of heartbeats of each heartbeat type in the N sub-RR intervals; and the number of heartbeats of each heartbeat type and the heartbeat types in the N sub-RR intervals are displayed in the form of the distribution diagram. The RR interval ECG data distribution display method can intuitively reflect the distribution, distribution ratios and corresponding ranges of various heartbeat types, thereby visually displaying the heartbeat information of the RR interval, providing a reference for doctors' decision-making on heart rhythm events, and improving the efficiency of doctors' diagnosis of the heart rhythm events.

BRIEF DESCRIPTION OF THE DRAWINGS

In order to describe the technical solutions in the embodiments of the present application or the prior art more clearly, the following will briefly introduce the drawings that need to be used in the description of the embodiments or the prior art. Obviously, the drawings in the following description are only some embodiments of the present application. Those of ordinary skill in the art can obtain other drawings based on these drawings without creative work.

Wherein.

DESCRIPTION OF THE EMBODIMENTS

The following will clearly and completely describe the technical solutions in the embodiments of the present disclosure with reference to the accompanying drawings in the embodiments of the present disclosure. Obviously, the described embodiments are only a part of the embodiments of the present invention, rather than all the embodiments. Based on the embodiments of the present disclosure, all other embodiments obtained by those of ordinary skill in the art without creative work shall fall within the protection scope of the present disclosure.

Figure 1:
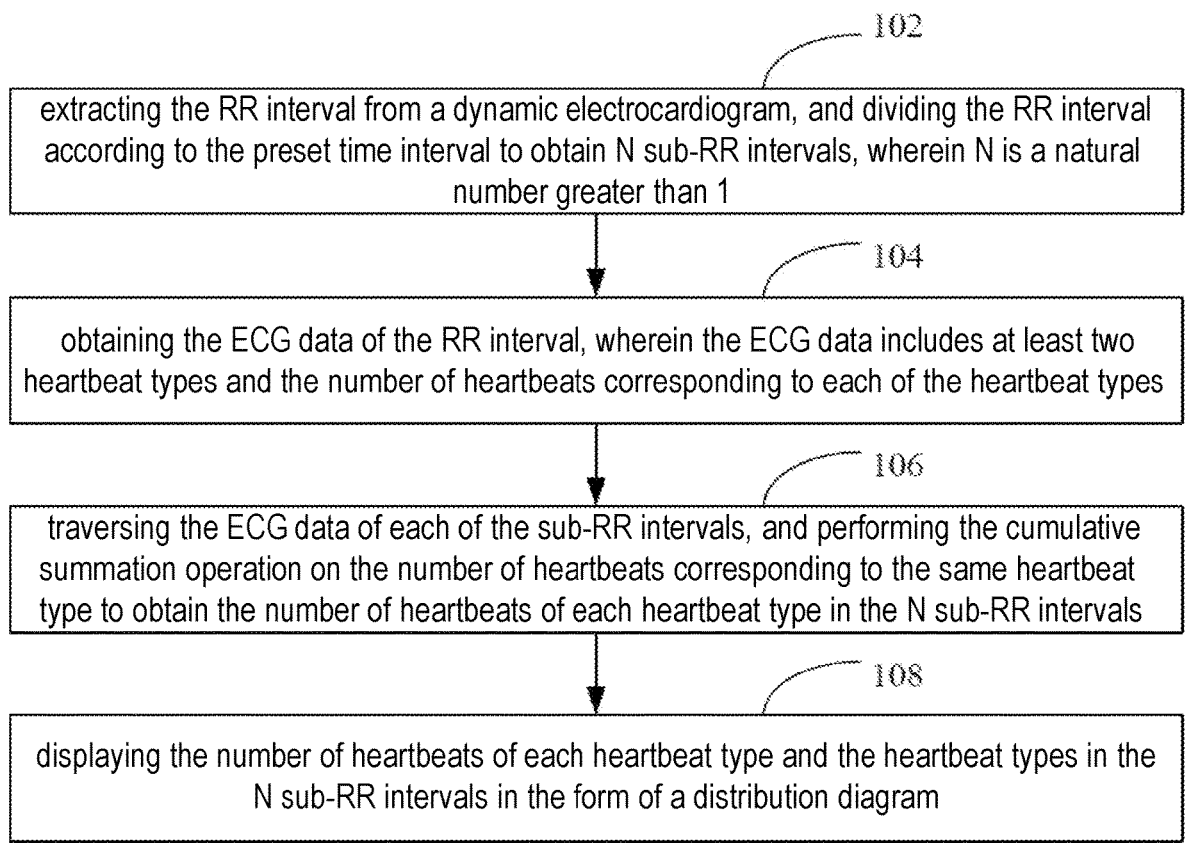
FIG. 1 is a flowchart diagram of an RR interval ECG data distribution display method in an embodiment.

As shown in FIG. 1, in one embodiment, an RR interval ECG data distribution display method is provided, and can be applied to a terminal or a server, the embodiment is illustrated through application of the embodiment to the server, and the RR interval ECG data distribution display method specifically includes the following steps of: In step 102, extracting the RR interval from a dynamic electrocardiogram, and dividing an RR interval according to a preset time interval to obtain N sub-RR intervals, wherein N is a natural number greater than 1.

Wherein, the dynamic electrocardiogram is used for reflecting the changes of an ECG signal within a period of time (such as 24 hours), and can be obtained through a dynamic electrocardiogram analyzer (such as Holter worn by a user). The RR interval refers to the time limit between two adjacent R waves in the QRS wave complex on the electrocardiogram, and is used as a basic parameter for doctors in clinical diagnosis of heart rhythm time. The N sub-RR intervals are obtained by dividing the RR interval according to the preset time interval. N is the number of the sub-RR intervals after division. Exemplarily, the preset time interval is 30 ms, and the RR interval time limit is 0.9 second, if each 30 ms is used as a sub-RR interval of the RR interval, 30 sub-RR intervals can be obtained, wherein the time limit interval of the first sub-RR interval is [0 ms, 30 ms], the time limit interval of the second sub RR interval is [31 ms, 60 ms] . . . , and the time limit interval of the 30th sub RR interval is [871 ms, 900 ms]. Understandably, the ECG information contained in the sub-RR intervals is more comprehensive, therefore, the RR interval is divided into the multiple sub-RR intervals, so that subsequent further analysis and processing based on the sub-RR intervals are performed, and the accuracy of analyzing first-point data corresponding to the RR interval is improved.

In step 104, obtaining the ECG data of the RR interval, wherein the ECG data includes at least two heartbeat types and the number of heartbeats corresponding to each of the heartbeat types.

Wherein, the ECG data is used for reflecting heartbeat information, and includes the heartbeat types and the number of heartbeats corresponding to the heartbeat types; illustratively, the heartbeat types can be determined by analyzing the origin of the heartbeats, and may include, but are not limited to five types: a normal heartbeat type, a sinus heartbeat type, an atrial heartbeat type, an atrioventricular junction heartbeat type and a ventricular heartbeat type. The ECG data of the RR interval includes the at least two heartbeat types; the number of heartbeats corresponding to each heartbeat type is obtained through frequency statistics in advance; and the number of heartbeats can reflect the degree of influence of the heartbeat type.

In step 106, traversing the ECG data of the RR interval, and performing the cumulative summation operation on the number of heartbeats corresponding to the same heartbeat type to obtain the number of heartbeats of each heartbeat type in the N sub-RR intervals.

Specifically, each sub-RR interval is used as a statistical unit, each sub-RR interval is traversed, and the number of heartbeats corresponding to the same heartbeat type in each sub-RR interval is accumulatively summated to obtain the number of heartbeats of various heartbeat types in each sub-RR interval. Understandably, the number of heartbeats of each heartbeat type in each sub-RR interval is obtained by calculation, so that the doctor can make a decision on heart rhythm events by comparing the number of heartbeats corresponding to various heartbeat types, and thus, decision-making basis is provided for the doctor.

In step 108, displaying the number of heartbeats of each heartbeat type and the heartbeat types in the N sub-RR intervals in the form of a distribution diagram.

Wherein, the distribution diagram can show the spatial distribution position and range of some phenomena; the distribution diagram in this embodiment is used for reflecting the association relationship between each heartbeat type in each sub-RR interval and the number of heartbeats corresponding to each heartbeat type; and understandably, the number of heartbeats of each heartbeat type and the heartbeat types in the N sub-RR intervals are displayed in the form of the distribution diagram, which can intuitively reflect the distribution, distribution ratios and corresponding ranges of various heartbeat types, thereby visually showing the heartbeat information of the RR interval, providing a reference for doctors' decision-making on heart rhythm events, and improving the efficiency of doctors' diagnosis of heart rhythm events.

According to the above RR interval ECG data distribution display method, the N sub-RR intervals are obtained by extracting the RR interval from the dynamic electrocardiogram, and dividing the RR interval according to the preset time interval; the ECG data of the RR interval is obtained, and includes the at least two heartbeat types and the number of heartbeats corresponding to each of the heartbeat types; the ECG data of each of the sub-RR intervals is traversed, and the cumulative summation operation is performed on the number of heartbeats corresponding to the same heartbeat type to obtain the number of heartbeats of each heartbeat type in the N sub-RR intervals; and the number of heartbeats of each heartbeat type and the heartbeat types in the N sub-RR intervals are displayed in the form of the distribution diagram. The RR interval ECG data distribution display method can intuitively reflect the distribution, distribution ratios and corresponding ranges of various heartbeat types, thereby visually displaying the heartbeat information of the RR interval, providing a reference for doctors' decision-making on heart rhythm events, and improving the efficiency of doctors' diagnosis of the heart rhythm events.

Figure 2:
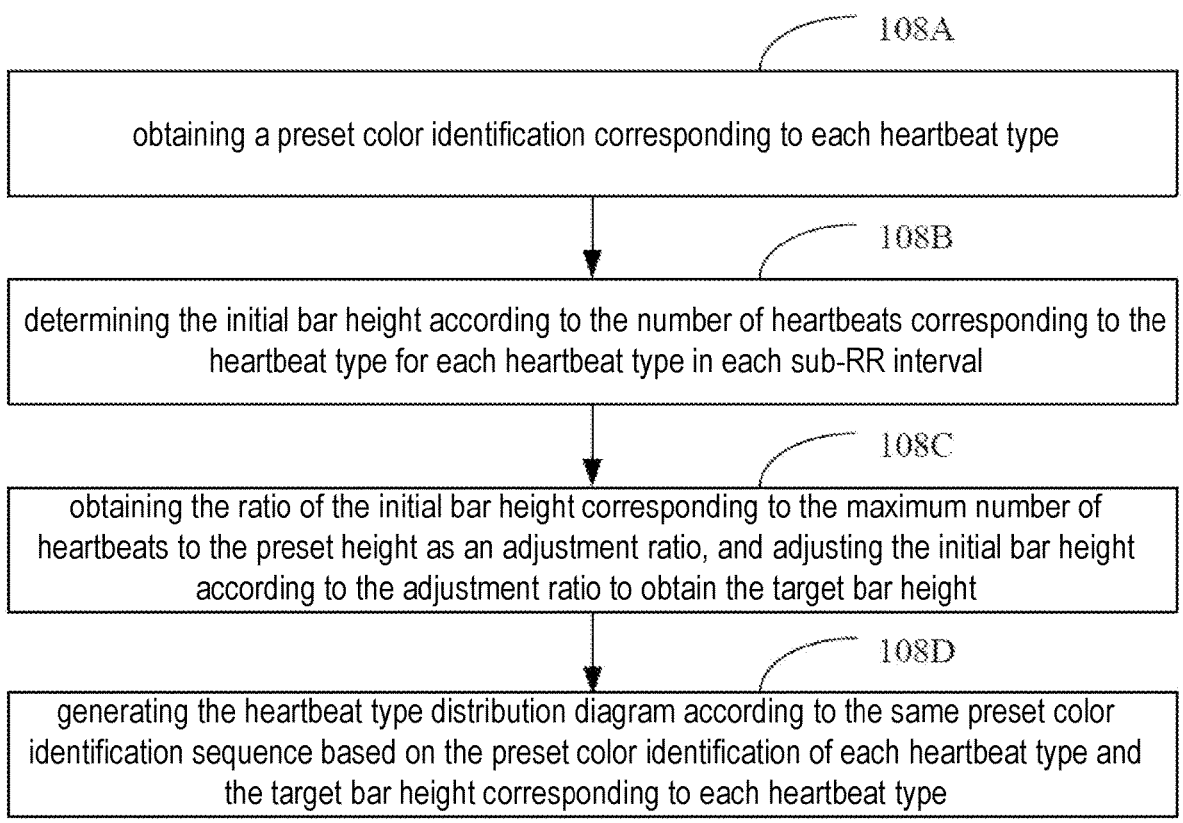
FIG. 2 is a flowchart diagram of a heartbeat type distribution diagram generation method in an embodiment.

As shown in FIG. 2, in one embodiment, the number of heartbeats of each heartbeat type and the heartbeat types in the N sub-RR intervals are displayed in the form of the distribution diagram, and a heartbeat type distribution diagram generation method includes the following steps of:

In step 108A, obtaining a preset color identification corresponding to each heartbeat type.

In step 108B, determining the initial bar height according to the number of heartbeats corresponding to the heartbeat type for each heartbeat type in each sub-RR interval.

In step 108C, obtaining the ratio of the initial bar height corresponding to the maximum number of heartbeats to the preset height as an adjustment ratio, and adjusting the initial bar height according to the adjustment ratio to obtain the target bar height.

In step 108D, generating the heartbeat type distribution diagram according to the same preset color identification sequence based on the preset color identification of each heartbeat type and the target bar height corresponding to each heartbeat type.

In this embodiment, each heartbeat type is configured with a different color identification for marking. The preset color identification corresponding to each heartbeat type can be obtained from the pre-configured comparison table of the heartbeat types and the color identifications. Then, the heartbeat types in each sub-RR interval and the number of heartbeats corresponding to each heartbeat type are obtained, and the bar height is determined according to the numbers of heartbeats. The adjustment ratio can ensure that the target bar height is within a limited range. For example, the default graphic display interface is 15 grids, the maximum initial bar height is 100 grids, the minimum initial bar height is 50 grids, the maximum initial bar height can be adjusted to be 15 grids through the adjustment ratio, and the minimum initial bar height can be adjusted to be 7.5 grids through the adjustment ratio; when the default number of heartbeats is 10, the corresponding bar height is 1 grid, and the display interface can display a maximum of 10 grids; when the numbers of heartbeats corresponding to the three heartbeat types are 150, 80, and 100 respectively, the corresponding initial bar heights are 15, 8 and 10 respectively, at this time, incomplete display exists, and therefore, some adjustments need to be made, the ratio of the initial bar height corresponding to the maximum number of heartbeats to the preset height is 15:10=1.5, and the initial bar heights 15, 8, and 10 are adjusted to 10, 5.3 and 6.7 respectively, that is, the target bar heights are 10, 5.3 and 6.7 respectively. The preset color identification sequence refers to the sequence of color identifications corresponding to multiple heartbeat types in each sub-RR interval, for example, the preset color identifications of a normal heartbeat type, a sinus heartbeat type, an atrial heartbeat type, an atrioventricular junction heartbeat type, and a ventricular heartbeat type are respectively red, green, yellow, blue, and black. If the target bars of one of the sub-RR intervals are red, green, yellow, blue, and black in order from low to high, the target bars of the other N−1 sub-RR intervals should also be drawn in this order. Understandably, the heartbeat type distribution diagram is generated through the same preset color identification sequence, so that the overall coordination of the heartbeat type distribution diagram is ensured, the heartbeat type distribution diagram is more in line with the habit of viewing the distribution diagram, the efficiency of the doctor to view the heartbeat type distribution diagram is improved, and the heartbeat type distribution diagram is also more intuitive and clearer.

Figure 3:
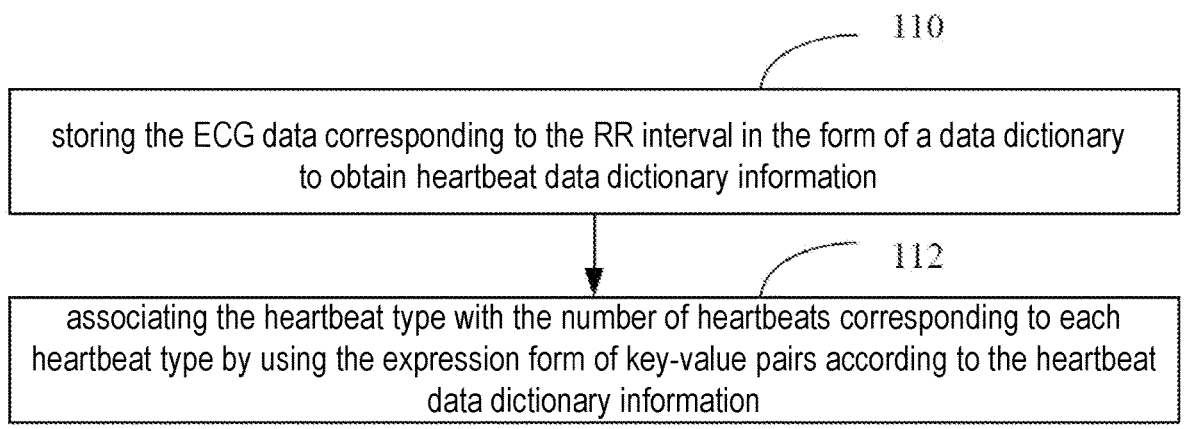
FIG. 3 is a flowchart diagram of an RR interval ECG data distribution display method in another embodiment.

As shown in FIG. 3, in one embodiment, after the ECG data of the RR interval is obtained, wherein the ECG data includes the at least two heartbeat types and the number of heartbeats corresponding to each heartbeat type, the RR interval ECG data distribution display method further includes the following steps of:

step 110, storing the ECG data corresponding to the RR interval in the form of a data dictionary to obtain heartbeat data dictionary information.

In step 112, associating the heartbeat type with the number of heartbeats corresponding to each heartbeat type by using the expression form of key-value pairs according to the heartbeat data dictionary information.

In this embodiment, the data dictionary refers to a collection of descriptions of data objects or items in a data model. The heartbeat data dictionary information in this embodiment is used for describing the corresponding relationship between each heartbeat type and the number of heartbeats corresponding to each heartbeat type to facilitate the management of the ECG data of the RR interval and improve the efficiency of the ECG data processing. The heartbeat data dictionary information is associated by adopting the expression form of key-value pairs, so that the heartbeat type and the number of heartbeats corresponding to each heartbeat type are quickly and conveniently associated, and the subsequent query and extraction operation of the heartbeat types and the number of heartbeats corresponding to each heartbeat type are also facilitated.

Figure 4:
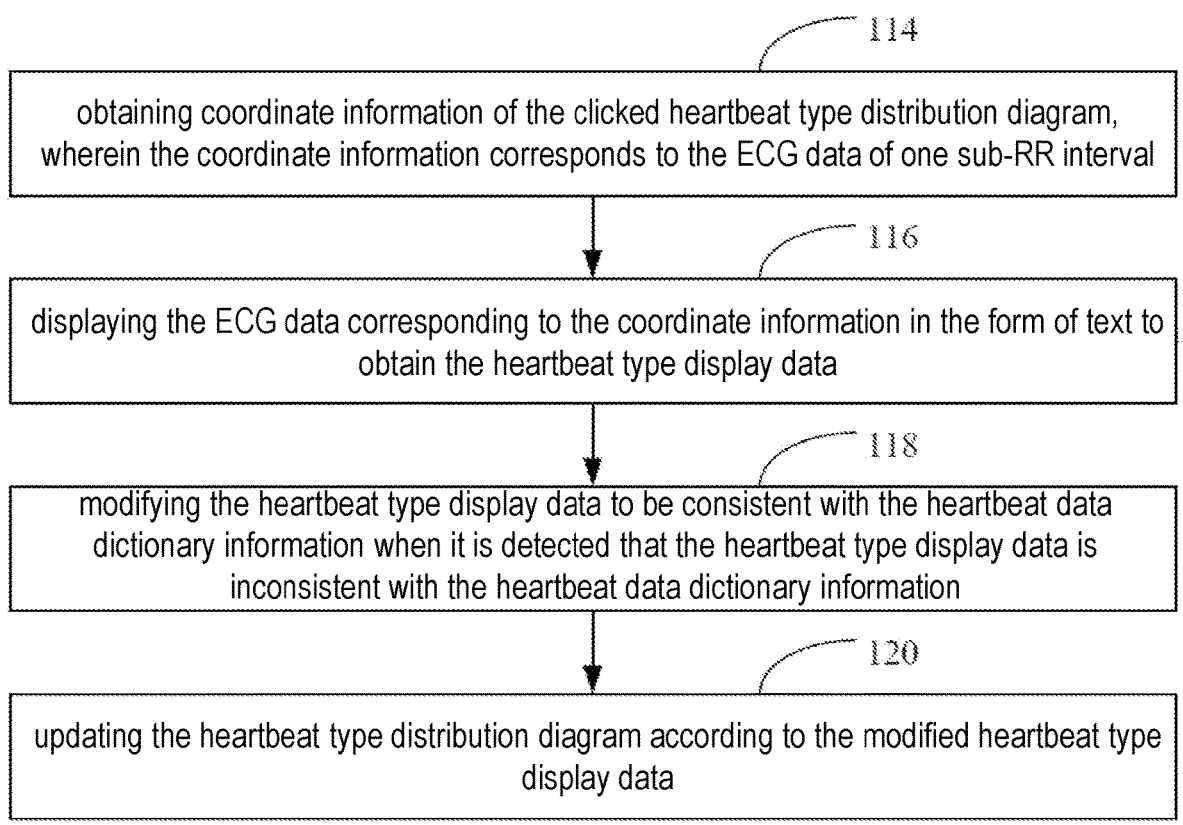
FIG. 4 is a flowchart diagram of a heartbeat type distribution diagram generation method in another embodiment.

As shown in FIG. 4, in one embodiment, after the heartbeat type distribution diagram is generated according to the same preset color identification sequence based on the preset color identification of each heartbeat type and the target bar height corresponding to each heartbeat type, the heartbeat type distribution diagram generation method further includes the following steps of:

In step 114, obtaining coordinate information of the clicked heartbeat type distribution diagram, wherein the coordinate information corresponds to the ECG data of one sub-RR interval;

In step 116, displaying the ECG data corresponding to the coordinate information in the form of text to obtain the heartbeat type display data;

In step 118, modifying the heartbeat type display data to be consistent with the heartbeat data dictionary information when it is detected that the heartbeat type display data is inconsistent with the heartbeat data dictionary information;

In step 120, updating the heartbeat type distribution diagram according to the modified heartbeat type display data.

In this embodiment, after the heartbeat type distribution diagram is generated, the reverse viewing of the ECG data of any sub RR interval in the heartbeat type distribution diagram is also supported, that is, the coordinate information of the user's click operation is obtained, and then, the ECG data of the sub-RR interval is displayed in the form of text. In a specific embodiment, when the sub-RR interval corresponding to the coordinate information is [391 ms, 420 ms], the distribution information of the sub-RR interval is displayed in the form of text. For example, in the sub-RR interval of [391 ms, 420 ms], the total heartbeat number: 1000, N (normal heartbeat type): 800 (80%), S (atrial heartbeat type): 50 (5%), V (ventricular heartbeat type): 100 (10%) . . . )".

Further, the heartbeat type display data can be compared with the heartbeat data dictionary information. If it is inconsistent, the heartbeat type distribution diagram can be reversely edited, the heartbeat type display data is modified to be consistent with the heartbeat data dictionary information, and the heartbeat type distribution diagram is updated according to the modified heartbeat type display data. Understandably, the heartbeat type distribution diagram in this embodiment can not only be reversely viewed, but can also be edited, so that the accuracy of the ECG data is ensured, and the efficiency of the doctor's processing of the ECG data is greatly improved.

Figure 5:
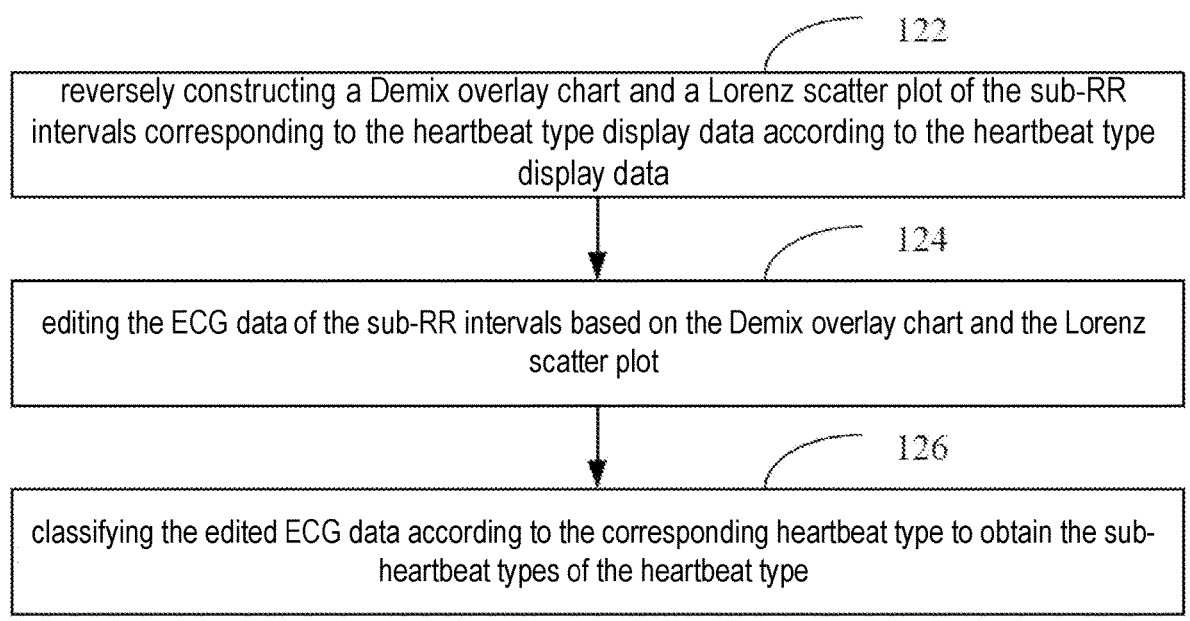
FIG. 5 is a flowchart diagram of an RR interval ECG data distribution display method in one more embodiment.

As shown in FIG. 5, in one embodiment, after the ECG data corresponding to the coordinate information is displayed in the form of text to obtain the heartbeat type display data, the RR interval ECG data distribution display method further includes the following steps of:

in step 122, reversely constructing a Demix overlay chart and a Lorenz scatter plot of the sub-RR intervals corresponding to the heartbeat type display data according to the heartbeat type display data;

in step 124, editing the ECG data of the sub-RR intervals based on the Demix overlay chart and the Lorenz scatter plot;

in step 126, classifying the edited ECG data according to the corresponding heartbeat type to obtain the sub-heartbeat types of the heartbeat type.

In this embodiment, firstly, the Demix overlay chart and the Lorenz scatter plot of the sub-RR intervals corresponding to the heartbeat type display data are reversely constructed. The Demix (waveform de-aliasing) overlay chart is a mixed waveform chart obtained by superimposing different heartbeat types. The Lorenz scatter plot (Lorenz plot) is a dot plot that reflects the changes of the adjacent sub-RR intervals, and marks the positions of the ECG data of all the adjacent sub-RR intervals on rectangular coordinates. Both the Demix overlay chart and the Lorenz scatter plot can be obtained through reverse construction of the heartbeat type display data. Then, the heartbeat types of the sub-RR interval can be subjected to secondary editing through the waveform and the distribution ratio of the ECG data of each sub-RR interval in the RR interval, and the edited ECG data is classified according to the corresponding heartbeat types to obtain the sub-heartbeat types of the heartbeat types. That is, each heartbeat type is subdivided into multiple sub-heartbeat types. For example, one sub-RR interval is [391 ms, 420 ms], and the number of heartbeats corresponding to the normal heartbeat type in the sub-RR interval is 40%; the other sub-RR interval is [421 ms, 450 ms], and the number of heartbeats corresponding to the normal heartbeat type in the other sub-RR interval is 20%; the normal heartbeat type in the sub-RR interval of [391 ms, 420 ms] can be defined as the normal heartbeat type of grade IV; and the normal heartbeat type in the sub-RR interval of [421 ms, 450 ms] can be defined as the normal heartbeat type of grade II. By dividing each heartbeat type into multiple sub-heartbeat types, the more in-depth analysis and statistics of the ECG data are realized, the depth of the ECG data analysis of the RR interval is improved, and more accurate reference is provided for the doctor's diagnosis of the heart rhythm events.

Figure 6:
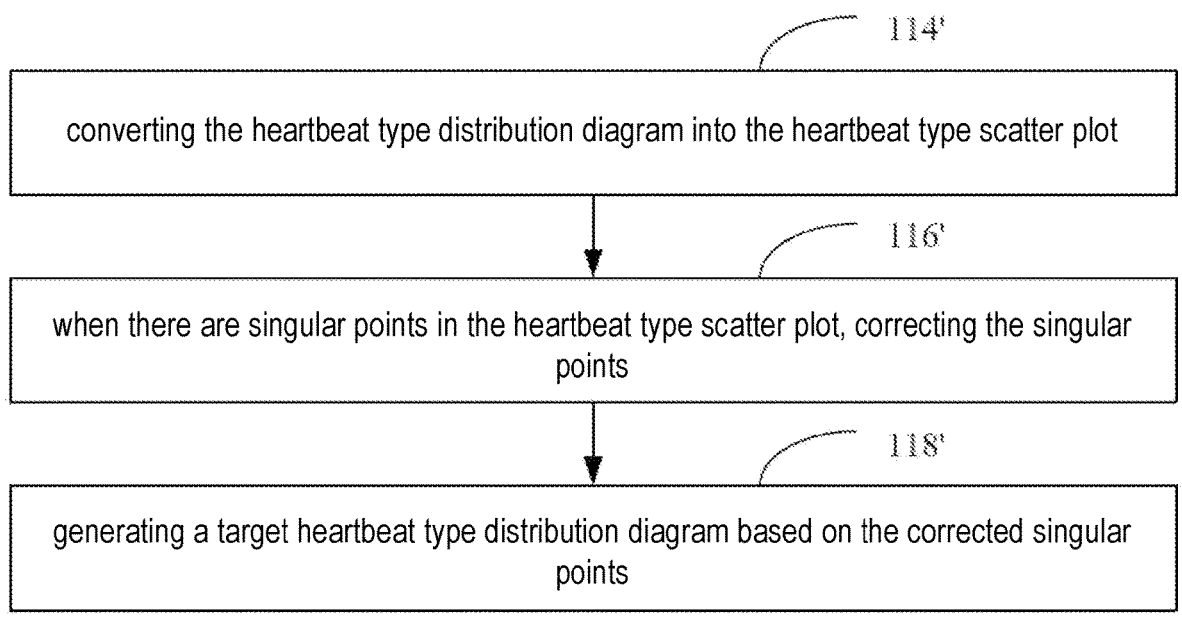
FIG. 6 is a flowchart diagram of a heartbeat type distribution diagram generation method in one more embodiment.

As shown in FIG. 6, in one embodiment, after the heartbeat type distribution diagram is generated according to the preset color identification of each heartbeat type and the target bar height corresponding to each heartbeat type, the heartbeat type distribution diagram generation method further includes the following steps of:

in step 114', converting the heartbeat type distribution diagram into the heartbeat type scatter plot;

in step 116', when there are singular points in the heartbeat type scatter plot, correcting the singular points;

in step 118', generating a target heartbeat type distribution diagram based on the corrected singular points.

In this embodiment, the heartbeat type scatter plot shows the distribution of ECG data in a two-dimensional coordinate system in a way of point distribution, and therefore, the singular points can be quickly searched according to the sparseness of each point in the heartbeat type scatter plot; the singular points refers to the points corresponding to the inaccurate ECG data; the points which are deviated from the center position of the heartbeat type scatter plot and reach the preset range are recognized as the singular points; the singular points are corrected by comparing the heartbeat type distribution diagrams; and then the target heartbeat type distribution diagram is generated based on the corrected singular points, and thus, the accuracy of the target heartbeat type distribution diagram is ensured.

Figure 7:
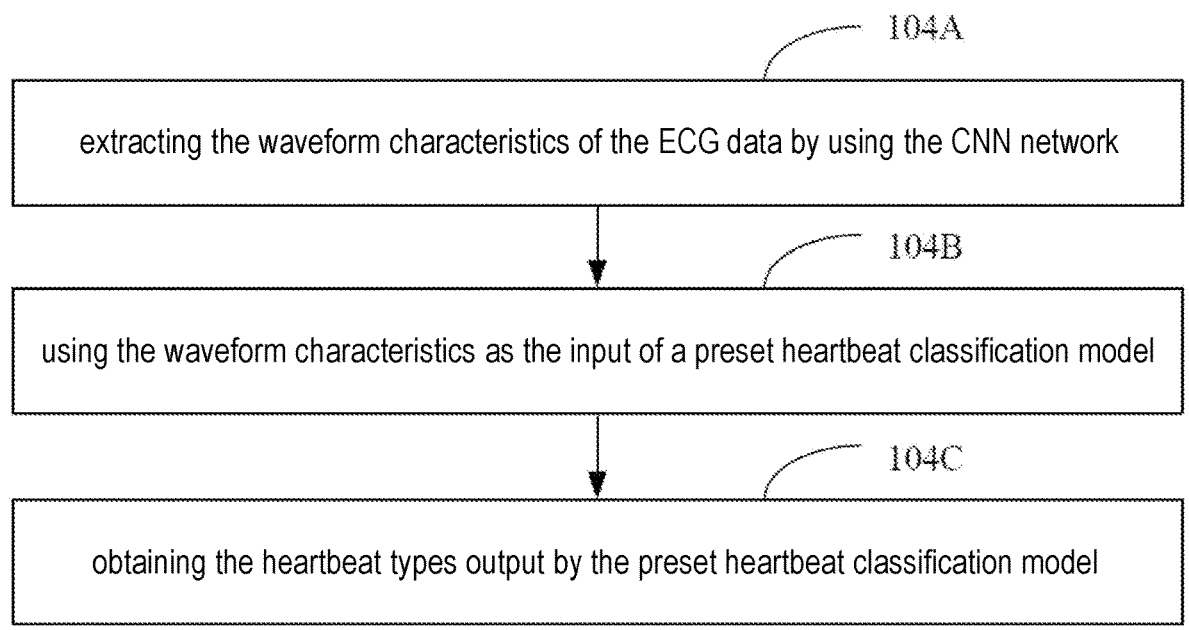
FIG. 7 is a flowchart diagram of a heartbeat type classification method in an embodiment.

As shown in FIG. 7, in one embodiment, the ECG data of the RR interval is obtained and includes the at least two heartbeat types and the number of heartbeats corresponding to each heartbeat type, and a heartbeat type classification method includes the following steps of:

in step 104A, extracting the waveform characteristics of the ECG data by using the CNN network;

in step 104B, using the waveform characteristics as the input of a preset heartbeat classification model;

in step 104C, obtaining the heartbeat types output by the preset heartbeat classification model.

In this embodiment, the preset heartbeat classification model is a pre-trained heartbeat type classification model. The waveform characteristics of the ECG data corresponding to different heartbeat types can be obtained as training samples, wherein the heartbeat types include a normal heartbeat type, a sinus heartbeat type, an atrial heartbeat type, an atrioventricular junction heartbeat type, and a ventricular heartbeat type. The model is obtained by algorithm training based on deep learning. By using the known heartbeat types to train the heartbeat classification model, the difficulty of obtaining training samples is reduced. The CNN (Convolutional Neural Networks), which is a deep learning method with robustness of a multi-layer hierarchical structure network, is used for extracting the waveform characteristics of the ECG data. The waveform characteristics are used as the input of the preset heartbeat classification model, and the heartbeat types output by the preset heartbeat classification model are used as the heartbeat types of the ECG data, and thus, the classification of the heartbeat types of the ECG data is realized.

Figure 8:
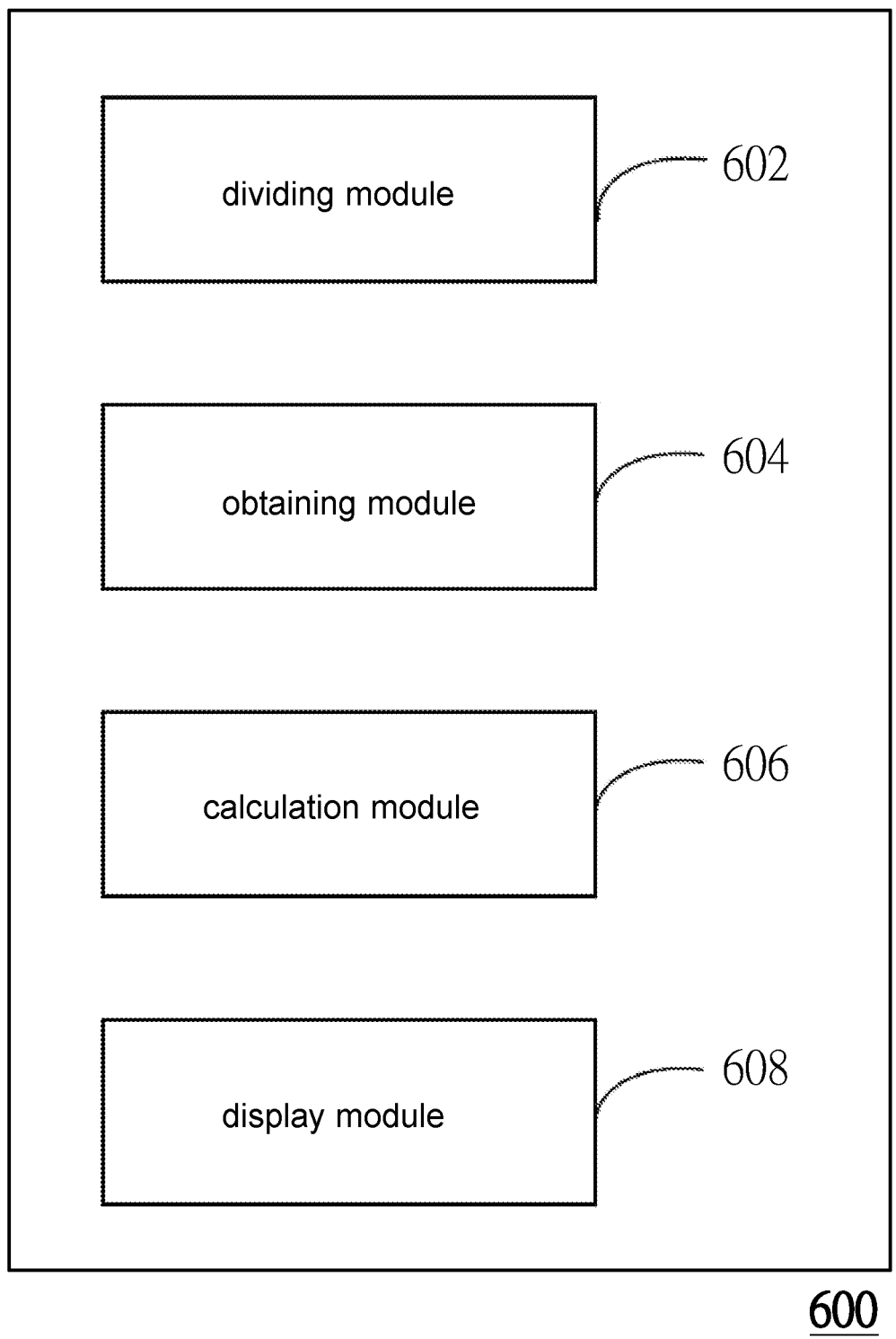
FIG. 8 is a structural block diagram of an RR interval ECG data distribution display device in an embodiment.

As shown in FIG. 8, in one embodiment, an RR interval ECG data distribution display device 600 is provided, and includes a dividing module 602, used for extracting the RR interval from the dynamic electrocardiogram, and dividing the RR interval according to a preset time interval to obtain the N sub-RR intervals, wherein N is a natural number greater than 1;

an obtaining module 604, used for obtaining the ECG data of the RR interval, wherein the ECG data includes the at least two heartbeat types and the number of heartbeats corresponding to each of the heartbeat types;

a calculation module 606, used for traversing the ECG data of each of the sub-RR intervals, and performing the cumulative summation operation on the number of heartbeats corresponding to the same heartbeat type to obtain the number of heartbeats of each heartbeat type in the N sub-RR intervals; and a display module 608, used for displaying the number of heartbeats of each heartbeat type and the heartbeat types in the N sub-RR intervals in the form of the distribution diagram.

In one embodiment, the display module includes an identification unit, a height calculation unit, a height adjustment unit, and a distribution diagram generation unit.

The identification unit is used for obtaining a preset color identification corresponding to each heartbeat type.

The height calculation unit is used for determining the initial bar height according to the number of heartbeats corresponding to the heartbeat type for each heartbeat type in each sub-RR interval.

The height adjustment unit is used for obtaining the ratio of the initial bar height corresponding to the maximum number of heartbeats to the preset height as an adjustment ratio, and adjusting the initial bar height according to the adjustment ratio to obtain the target bar height.

The distribution diagram generation unit is used for generating the heartbeat type distribution diagram according to the same preset color identification sequence based on the preset color identification of each heartbeat type and the target bar height corresponding to each heartbeat type.

In one embodiment, the device further includes a data processing module and a data association module.

The data processing module is used for storing the ECG data of the RR interval in the form of a data dictionary to obtain heartbeat data dictionary information.

The data association module is used for associating the heartbeat type with the number of heartbeats corresponding to each heartbeat type by using the expression form of key-value pairs according to the heartbeat data dictionary information.

In one embodiment, the device further includes an information obtaining module, an information display module, an information detection module, and an updating module.

The information obtaining module is used for obtaining coordinate information of the clicked heartbeat type distribution diagram, wherein the coordinate information corresponds to the ECG data of a sub-RR interval.

The information display module is used for displaying the ECG data corresponding to the coordinate information in the form of text to obtain the heartbeat type display data.

The information detection module is used for modifying the heartbeat type display data to be consistent with the heartbeat data dictionary information when it is detected that the heartbeat type display data is inconsistent with the heartbeat data dictionary information.

The updating module is used for updating the heartbeat type distribution diagram according to the modified heartbeat type display data.

In one embodiment, the device further includes a diagram constructing module, a diagram editing module, and a data subdivision module.

The diagram construction module is used for reversely constructing the Demix overlay chart and the Lorenz scatter plot of the sub-RR intervals corresponding to the heartbeat type display data according to the heartbeat type display data.

The diagram editing module is used for editing the ECG data of the sub-RR intervals based on the Demix overlay chart and the Lorenz scatter plot.

The data subdivision module is used for classifying the edited ECG data according to the corresponding heartbeat type to obtain the sub-heartbeat types of the heartbeat type.

In one embodiment, the obtaining module includes a characteristic extraction unit, a characteristic classification unit, and a result obtaining unit.

The characteristic extraction unit is used for extracting the waveform characteristic of the ECG data by using the CNN network.

The characteristic classification unit is used for using the waveform characteristics as the input of the preset heartbeat classification model.

The result obtaining unit is used for obtaining the heartbeat types output by the preset heartbeat classification model.

Figure 9:
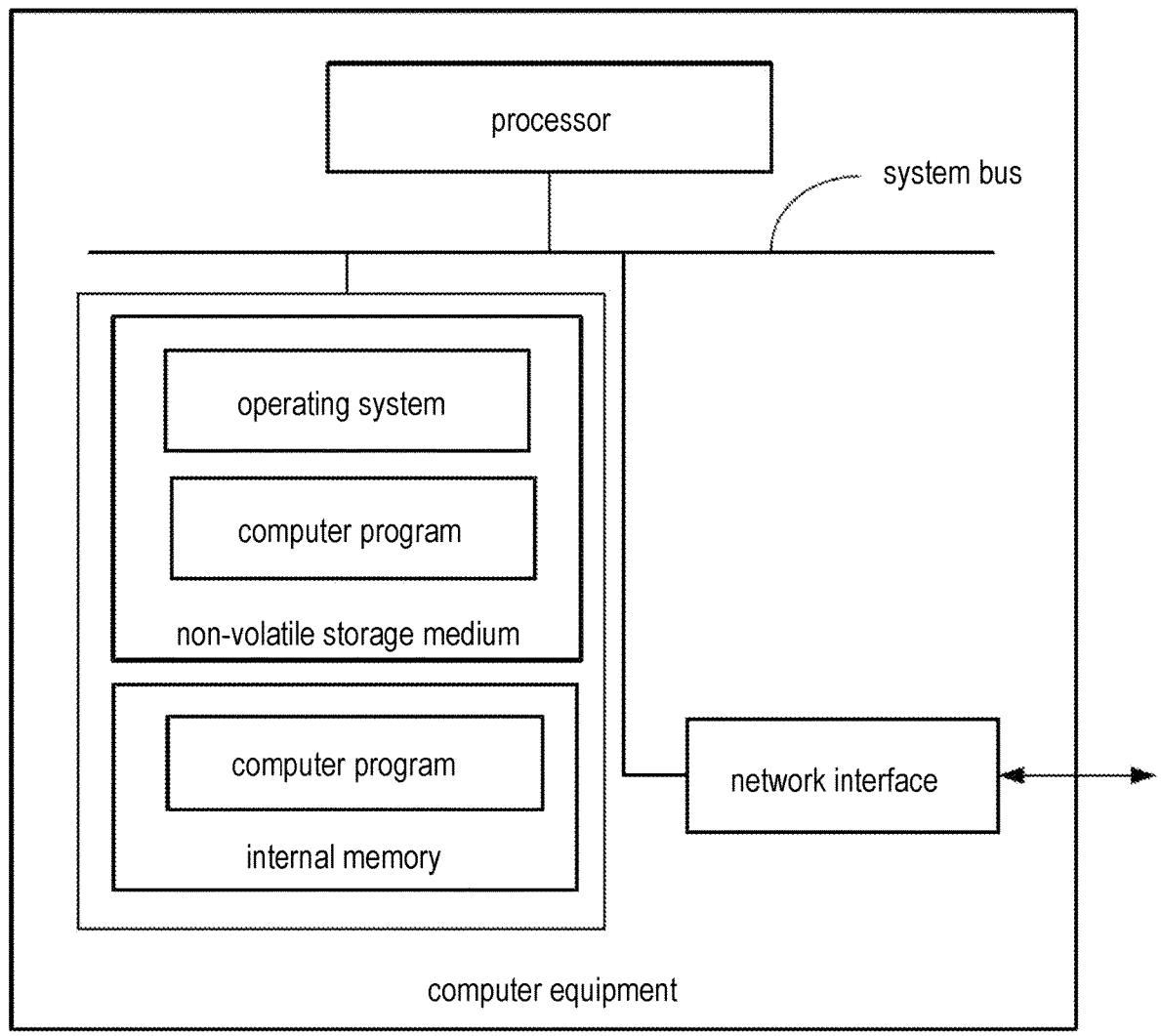
FIG. 9 is a structural block diagram of computer equipment in an embodiment.

FIG. 9 shows an internal structure diagram of computer equipment in one embodiment. The computer equipment may specifically be a server, and the server includes, but is not limited to a high-performance computer and a high-performance computer cluster. As shown in FIG. 9, the computer equipment includes a processor, a memory, and a network interface which are connected through a system bus. The memory includes a non-volatile storage medium and an internal memory. The non-volatile storage medium of the computer equipment stores an operating system and may also store a computer program, and when the computer program is executed by the processor, the processor can realize the RR interval ECG data distribution display method. The internal memory may also store the computer program, and when the computer program is executed by the processor, the processor can execute the RR interval ECG data distribution display method. Those skilled in the art can understand that the structure shown in FIG. 9 is only a block diagram of a part of the structure related to the solution of the present application, and does not constitute a limitation on the computer equipment to which the solution of the present application is applied. The specific computer equipment may include more or fewer parts than shown in the figure, or certain combining parts, or have different part arrangements.

In one embodiment, the RR interval ECG data distribution display method provided by the present application can be implemented in the form of a computer program, and the computer program can run on the computer equipment as shown in FIG. 9. The memory of the computer equipment can store various program templates that make up the RR interval ECG data distribution display device, for example, the dividing module 602, the obtaining module 604, the calculation module 606, and the display module 608.

Computer equipment includes a memory, a processor, and a computer program stored in the memory and running on the processor. When the computer program is executed by the processor, the implemented steps are as follows: extracting the RR interval from the dynamic electrocardiogram, and dividing the RR interval according to a preset time interval to obtain N sub-RR intervals, wherein N is a natural number greater than 1; obtaining the ECG data of the RR interval, wherein the ECG data includes the at least two heartbeat types and the number of heartbeats corresponding to each of the heartbeat types; traversing the ECG data of each of the sub-RR intervals, and performing the cumulative summation operation on the number of heartbeats corresponding to the same heartbeat type to obtain the number of heartbeats of each heartbeat type in the N sub-RR intervals; and displaying the number of heartbeats of each heartbeat type and the heartbeat types in the N sub-RR intervals in the form of the distribution diagram.

In one embodiment, the number of heartbeats of each heartbeat type and and the heartbeat types in the N sub-RR intervals are displayed in the form of the distribution diagram, and the implemented steps are as follows: obtaining the preset color identification corresponding to each heartbeat type; determining the initial bar height according to the number of heartbeats corresponding to the heartbeat type for each heartbeat type in each sub-RR interval; obtaining the ratio of the initial bar height corresponding to the maximum number of heartbeats to the preset height as an adjustment ratio, and adjusting the initial bar height according to the adjustment ratio to obtain the target bar height; and generating the heartbeat type distribution diagram according to the same preset color identification sequence based on the preset color identification of each heartbeat type and the target bar height corresponding to each heartbeat type.

In one embodiment, after the ECG data of the RR interval is obtained, wherein the ECG data includes the at least two heartbeat types and the number of heartbeats corresponding to each heartbeat type, the RR interval ECG data distribution display method further includes the following steps of: storing the ECG data corresponding to the RR interval in the form of the data dictionary to obtain heartbeat data dictionary information; and associating the heartbeat type with the number of heartbeats corresponding to each heartbeat type by using the expression form of key-value pairs according to the heartbeat data dictionary information.

In one embodiment, after the heartbeat type distribution diagram is generated according to the same preset color identification sequence based on the preset color identification of each heartbeat type and the target bar height corresponding to each heartbeat type, the heartbeat type distribution diagram generation method further includes the following steps of: obtaining coordinate information of the clicked heartbeat type distribution diagram, wherein the coordinate information corresponds to the ECG data of one sub-RR interval; displaying the ECG data corresponding to the coordinate information in the form of text to obtain the heartbeat type display data; modifying the heartbeat type display data to be consistent with the heartbeat data dictionary information when it is detected that the heartbeat type display data is inconsistent with the heartbeat data dictionary information; and updating the heartbeat type distribution diagram according to the modified heartbeat type display data.

In one embodiment, after the ECG data corresponding to the coordinate information is displayed in the form of text to obtain the heartbeat type display data, the RR interval ECG data distribution display method further includes the following steps of: reversely constructing a Demix overlay chart and a Lorenz scatter plot of the sub-RR intervals corresponding to the heartbeat type display data according to the heartbeat type display data; editing the ECG data of the sub-RR intervals based on the Demix overlay chart and the Lorenz scatter plot; and classifying the edited ECG data according to the corresponding heartbeat type to obtain the sub-heartbeat types of the heartbeat type.

In one embodiment, after the heartbeat type distribution diagram is generated according to the preset color identification of each heartbeat type and the target bar height corresponding to each heartbeat type, the heartbeat type distribution diagram generation method further includes the following steps of: converting the heartbeat type distribution diagram into a heartbeat type scatter plot; when there are singular points in the heartbeat type scatter plot, correcting the singular points; and generating a target heartbeat type distribution diagram based on the corrected singular points.

In one embodiment, the ECG data of the RR interval is obtained and includes the at least two heartbeat types and the number of heartbeats corresponding to each heartbeat type. The heartbeat type classification method includes the following steps of: extracting the waveform characteristics of the ECG data by using the CNN network; using the waveform characteristics as the input of a preset heartbeat classification model; and obtaining the heartbeat type output by the preset heartbeat classification model.

A computer-readable storage medium is provided; and the computer-readable storage medium stores the computer program and is characterized in that when the computer program is executed by the processor, the implemented steps are as follows: extracting the RR interval from the dynamic electrocardiogram, and dividing the RR interval according to the preset time interval to obtain N sub-RR intervals, wherein N is a natural number greater than 1; obtaining the ECG data of the RR interval, wherein the ECG data includes the at least two heartbeat types and the number of heartbeats corresponding to each of the heartbeat types; traversing the ECG data of each of the sub-RR intervals, and performing the cumulative summation operation on the number of heartbeats corresponding to the same heartbeat type to obtain the number of heartbeats of each heartbeat type in the N sub-RR intervals; and displaying the number of heartbeats of each heartbeat type and the heartbeat types in the N sub-RR intervals in the form of the distribution diagram.

In one embodiment, the number of heartbeats of each heartbeat type and and the heartbeat types in the N sub-RR intervals are displayed in the form of the distribution diagram, and the implemented steps are as follows: obtaining the preset color identification corresponding to each heartbeat type; determining the initial bar height according to the number of heartbeats corresponding to the heartbeat type for each heartbeat type in each sub-RR interval; obtaining the ratio of the initial bar height corresponding to the maximum number of heartbeats to the preset height as an adjustment ratio, and adjusting the initial bar height according to the adjustment ratio to obtain the target bar height; and generating the heartbeat type distribution diagram according to the same preset color identification sequence based on the preset color identification of each heartbeat type and the target bar height corresponding to each heartbeat type.

In one embodiment, after the ECG data of the RR interval is obtained, wherein the ECG data includes the at least two heartbeat types and the number of heartbeats corresponding to each heartbeat type, the RR interval ECG data distribution display method further includes the following steps of: storing the ECG data corresponding to the RR interval in the form of the data dictionary to obtain heartbeat data dictionary information; and associating the heartbeat type with the number of heartbeats corresponding to each heartbeat type by using the expression form of key-value pairs according to the heartbeat data dictionary information.

In one embodiment, after the heartbeat type distribution diagram is generated according to the same preset color identification sequence based on the preset color identification of each heartbeat type and the target bar height corresponding to each heartbeat type, the heartbeat type distribution diagram generation method further includes the following steps of: obtaining coordinate information of the clicked heartbeat type distribution diagram, wherein the coordinate information corresponds to the ECG data of one sub-RR interval; displaying the ECG data corresponding to the coordinate information in the form of text to obtain the heartbeat type display data; modifying the heartbeat type display data to be consistent with the heartbeat data dictionary information when it is detected that the heartbeat type display data is inconsistent with the heartbeat data dictionary information; and updating the heartbeat type distribution diagram according to the modified heartbeat type display data.

In one embodiment, after the ECG data corresponding to the coordinate information is displayed in the form of text to obtain the heartbeat type display data, the RR interval ECG data distribution display method further includes the following steps of: reversely constructing a Demix overlay chart and a Lorenz scatter plot of the sub-RR intervals corresponding to the heartbeat type display data according to the heartbeat type display data; editing the ECG data of the sub-RR interval based on the Demix overlay chart and the Lorenz scatter plot; and classifying the edited ECG data according to the corresponding heartbeat type to obtain the sub-heartbeat types of the heartbeat type.

In one embodiment, after the heartbeat type distribution diagram is generated according to the preset color identification of each heartbeat type and the target bar height corresponding to each heartbeat type, the heartbeat type distribution diagram generation method further includes the following steps of: converting the heartbeat type distribution diagram into the heartbeat type scatter plot; when there are singular points in the heartbeat type scatter plot, correcting the singular points; and generating the target heartbeat type distribution diagram based on the corrected singular points.

In one embodiment, the ECG data of the RR interval is obtained and includes the at least two heartbeat types and the number of heartbeats corresponding to each heartbeat type. The heartbeat type classification method includes the following steps of: extracting the waveform characteristics of the ECG data by using the CNN network; using the waveform characteristics as the input of a preset heartbeat classification model; and obtaining the heartbeat type output by the preset heartbeat classification model.

A person of ordinary skill in the art can understand that all or part of the processes in the methods of the foregoing embodiments can be implemented by instructing relevant hardware through the computer program. The program can be stored in a non-volatile computer readable storage medium. When the program is executed, it may include the processes of the above-mentioned method embodiments. Wherein, any reference to memory, storage, database, or other media used in the embodiments provided by the present application may include a non-volatile and/or volatile memory. The non-volatile memory may include a read-only memory (ROM), a programmable read-only memory (PROM), an electrically programmable read-only memory (EPROM), an electrically erasable programmable read-only memory (EEPROM), or a flash memory. The volatile memory may include a random-access memory (RAM) or an external cache memory. As an illustration and not a limitation, RAM is available in many forms, such as static RAM (SRAM), dynamic RAM (DRAM), synchronous DRAM (SDRAM), double data rate SDRAM (DDRS-DRAM), enhanced SDRAM (ESDRAM), synchronous link (Synchlink) DRAM (SLDRAM), memory bus (Rambus) direct RAM (RDRAM), direct memory bus dynamic RAM (DRDRAM), and memory bus dynamic RAM (RDRAM), etc.

The technical features of the above embodiments can be combined arbitrarily. In order to make the description concise, all possible combinations of the technical features in the above embodiments are not described. However, as long as there is no contradiction in the combination of these technical features, they should be considered to be within the scope described in this specification.

The above-mentioned embodiments only express several implementation manners of the present application, and the description is relatively specific and detailed, but it should not be construed as a limitation to the patent scope of the present application. It should be pointed out that several modifications and improvements can be made by those of ordinary skill in the art without departing from the concept of the present application, and these all fall within the protection scope of the present application. Therefore, the protection scope of the patent in the present application shall be subject to the appended claims.

What is claimed is:

1. An RR interval electrocardiography (ECG) data distribution display method, comprising:
   extracting, by a processor, an RR interval from a dynamic electrocardiogram, and dividing the RR interval according to a preset time interval to obtain N sub-RR intervals, wherein N is a natural number greater than 1;
   obtaining, by the processor, ECG data of the RR interval, wherein the ECG data includes at least two heartbeat types and a number of heartbeats corresponding to each of the heartbeat types, wherein each of the heartbeat types is determined by analyzing the heartbeats;

traversing, by the processor, ECG data of each of the sub-RR intervals, and performing a cumulative summation operation on the number of heartbeats corresponding to the same heartbeat type to obtain a number of heartbeats of each heartbeat type in the N sub-RR intervals;

displaying, by the processor, the number of heartbeats of each heartbeat type and the heartbeat types in the N sub-RR intervals in a form of a distribution diagram, further comprises:

obtaining, by the processor, a preset color identification corresponding to each heartbeat type;

determining, by the processor, a first initial bar height according to the number of heartbeats corresponding to the heartbeat type for a first heartbeat type in each sub-RR interval and a second initial bar height according to the number of heartbeats corresponding to the heartbeat type for a second heartbeat type in each of the sub-RR interval;

obtaining, by the processor, a ratio of the first initial bar height to a preset height as an adjustment ratio, and adjusting the first initial bar height according to the adjustment ratio to obtain a target bar height, wherein the first initial bar height has a maximum number of heartbeats, wherein the preset height is a maximum number of grids of a display interface; and generating, by the processor, a heartbeat type distribution diagram according to the same preset color identification sequence based on the preset color identification of each heartbeat type and the target bar height corresponding to each heartbeat type, wherein the distribution diagram corresponds to ranges of each of the heartbeat types; and controlling a display device, by the processor, to output D the heartbeat types for indicating on decision-making on heart rhythm events.

2. The RR interval ECG data distribution display method according to claim 1, wherein after obtaining the ECG data of the RR interval, wherein the ECG data includes the at least two heartbeat types and the number of heartbeats corresponding to each heartbeat type, the method further comprises:

storing, by the processor, the ECG data of the RR interval in a form of a data dictionary to obtain heartbeat data dictionary information; and associating, by the processor, the heartbeat type with the number of heartbeats corresponding to each heartbeat type by using an expression form of key-value pairs according to the heartbeat data dictionary information.

3. The RR interval ECG data distribution display method according to claim 1, wherein after generating the heartbeat type distribution diagram according to the same preset color identification sequence based on the preset color identification of each heartbeat type and the target bar height corresponding to each heartbeat type, the method further comprises:

obtaining, by the processor, coordinate information of a heartbeat type distribution diagram, wherein the coordinate information corresponds to the ECG data of one sub-RR interval, wherein the coordinate information corresponds to a user's click operation;

controlling the display device, by the processor, to display, the ECG data corresponding to the coordinate information in a form of text to obtain heartbeat type display data;

modifying, by the processor, the heartbeat type display data to be consistent with the heartbeat data dictionary information when it is detected that the heartbeat type display data is inconsistent with the heartbeat data dictionary information; and updating, by the processor, the heartbeat type distribution diagram according to the modified heartbeat type display data.

4. The RR interval ECG data distribution display method according to claim 3, wherein after displaying the ECG data corresponding to the coordinate information in the form of text to obtain the heartbeat type display data, the method further comprises:

reversely constructing, by the processor, a Demix overlay chart, which is a mixed waveform chart obtained by superimposing different heartbeat types, and a Lorenz scatter plot of the sub-RR intervals corresponding to the heartbeat type display data according to the heartbeat type display data;

editing, by the processor, the ECG data of the sub-RR intervals based on the Demix overlay chart and the Lorenz scatter plot; and classifying, by the processor, the edited ECG data according to the corresponding heartbeat type to obtain the sub-heartbeat types of the heartbeat type.

5. The RR interval ECG data distribution display method according to claim 1, wherein after generating the heartbeat type distribution diagram based on the preset color identification of each heartbeat type and the target bar height corresponding to each heartbeat type, the method further comprises:

converting, by the processor, the heartbeat type distribution diagram into a heartbeat type scatter plot;

correcting, by the processor, singular points, which correspond to inaccurate ECG data, when there are the singular points in the heartbeat type scatter plot; and generating, by the processor, a target heartbeat type distribution diagram based on the corrected singular points.

6. The RR interval ECG data distribution display method according to claim 1, wherein the step of obtaining the ECG data of the RR interval, wherein the ECG data includes the at least two heartbeat types and the number of heartbeats corresponding to each heartbeat type comprises:

using a CNN (Convolutional Neural Networks), by the processor, to extract wave form characteristics of the ECG data; using, by the processor, the waveform characteristics as an input of a preset heartbeat classification model; and obtaining, by the processor, the heartbeat types output by the preset heartbeat classification model.

7. An RR interval ECG data distribution display device, wherein the RR interval ECG data distribution display device comprises:

a dividing module, executed by a processor, the dividing module is configured to extract the RR interval from a dynamic electrocardiogram, and dividing the RR interval according to a preset time interval to obtain N sub-RR intervals, wherein N is a natural number greater than 1;

an obtaining module, executed by the processor, the obtaining module is configured to obtain ECG data of the RR interval, wherein the ECG data comprises the at least two heartbeat types and a number of heartbeats corresponding to each of the heartbeat types, wherein the each of the heartbeat types is determined by analyzing the heartbeats;

a calculation module, executed by the processor, the calculation module is configured to traverse ECG data of each of the sub-RR intervals, and performing a cumulative summation operation on the number of heartbeats corresponding to the same heartbeat type to obtain a number of heartbeats of each heartbeat type in the N sub-RR intervals;

a display device, controlled by the processor, to display the number of heartbeats of each heartbeat type and the heartbeat types in the N sub-RR intervals in a form of the distribution diagram, where the display device is further configured to:

obtain a preset color identification corresponding to each heartbeat type;

determine a first initial bar height according to the number of heartbeats corresponding to the heartbeat type for a first heartbeat type in each sub-RR interval and a second initial bar height according to the number of heartbeats corresponding to the heartbeat type for a second heartbeat type in each of the sub-RR interval;

obtain a ratio of the first initial bar height to a preset height as an adjustment ratio, and adjusting the first initial bar height according to the adjustment ratio to obtain a target bar height, wherein the first initial bar height has a maximum number of heartbeats, wherein the preset height is a maximum number of a display interface; and generate a heartbeat type distribution diagram according to the same preset color identification sequence based on the preset color identification of each heartbeat type and the target bar height corresponding to each heartbeat type, wherein the distribution diagram corresponds to ranges of each of the heartbeat types; and the display device is further configured to output the heartbeat types for indicating on decision-making on heart rhythm events.

8. A computer equipment, wherein the computer equipment comprises a memory, the processor, and a computer program stored in the memory and running on the processor, and when the computer program is executed, the steps of the RR interval ECG data distribution display method according to claim 1 is realized.

9. A non-transitory computer-readable storage medium, stored with a computer program, and wherein when the computer program is executed, the steps of the RR interval ECG data distribution display method according to claim 1 is realized.

* * * * *